United States Patent [19]

Cerny et al.

[11] Patent Number: 4,957,656
[45] Date of Patent: Sep. 18, 1990

[54] CONTINUOUS SONICATION METHOD FOR PREPARING PROTEIN ENCAPSULATED MICROBUBBLES

[75] Inventors: David Cerny, Chula Vista; Gary J. Mills; Peter J. Westkaemper, both of San Diego, all of Calif.

[73] Assignee: Molecular Biosystems, Inc., San Diego, Calif.

[21] Appl. No.: 244,844

[22] Filed: Sep. 14, 1988

[51] Int. Cl.⁵ .................. B01J 13/02; A61K 49/00
[52] U.S. Cl. .................. 252/311; 128/662.02; 424/9
[58] Field of Search .................. 252/307; 128/662.02; 106/122

[56] References Cited
U.S. PATENT DOCUMENTS

| | | | |
|---|---|---|---|
| 4,276,885 | 7/1981 | Tickner et al. | 128/662.02 |
| 4,466,442 | 8/1984 | Hilmann et al. | 128/660 X |
| 4,572,203 | 2/1986 | Feinstein | 128/661 |
| 4,718,433 | 1/1988 | Feinstein | 128/660 |
| 4,774,958 | 10/1988 | Feinstein | 128/660.01 |
| 4,832,941 | 5/1989 | Berwing et al. | 424/9 |
| 4,844,882 | 7/1989 | Widder et al. | 128/660.01 |

OTHER PUBLICATIONS

Keller, Feinstein, and Watson, *American Heart Journal*, vol. 114, No. 3, Sep. 1987, pp. 570–575.
Tickner and Rasor, National Technical Information Service Report, HR 62917–1A, Mar. 13, 1986, pp. 34–40.
Feinstein et al., JACC, vol. 3, No. 1, Jan. 1984, pp. 14–20.

*Primary Examiner*—Richard D. Lovering
*Assistant Examiner*—Daniel S. Metzmaier
*Attorney, Agent, or Firm*—Tilton, Fallon Lungmus & Chestnut

[57] ABSTRACT

An ultrasonic imaging agent is produced by a continuous sonication processing of an aqueous solution of heat-denaturable biocompatible protein. The solution is carefully preheated to a temperature of incipient protein denaturation without forming insolubilized protein. A gaseous fluid, preferably air, is added to the solution. In the sonication, the air-containing solution is foamed, increasing the formation and concentration of microbubbles, and the solution is further heated to insolubilize a portion of the protein, thereby encapsulating the microbubbles and forming particulate microspheres.

6 Claims, 3 Drawing Sheets

CONTINUOUS SONICATION METHOD FOR PREPARING PROTEIN ENCAPSULATED MICROBUBBLES

FIELD OF INVENTION

This invention relates to ultrasonic imaging of the human body for diagnostic purposes; and, more particularly, to the preparation of ultrasonic imaging agents by sonication of protein solutions.

BACKGROUND OF INVENTION

It has been known since 1968-70 that contrast echocardiography can be used to delineate intracardiac structures, assess valvular competence, demonstrate intracardiac shunts, and identify pericardial effusion. (Gramiak and Shah, 1968; and Feigenbaum, et al., 1970). Ultrasonic imaging of the heart potentially has important advantages of convenience, safety, and reduced cost over present diagnostic procedures, such as angiography, which requires the use of radio-opaque dyes for X-ray imaging, or the use of radio-nuclide imaging agents for radioimaging. However, progress in practical applications of ultrasonic imaging has been delayed by the lack of effective clinicallyusable imaging agents.

Ultrasonic imaging utilizes an ultrasonic scanner to generate and receive sound waves. The scanner is placed on a body surface overlying the area to be imaged, and sound waves are directed toward that area. The scanner detects reflected sound waves and translates that data into images. When ultrasonic energy is transmitted through a substance, the acoustic properties of the substance depend upon the velocity of the transmission and the density of the substance. Changes in the substance's acoustic properties (e.g., variations in acoustic impedance) are most prominent at the interfaces of different substances, such as a liquid-solid or liquid-gas interface. Consequently, when ultrasonic energy is directed through media, changes in acoustic properties will result in more intense sound reflection signals for detection by the ultrasonic scanner.

Ultrasonic imaging agents can consist of small solid or gaseous particles which, when injected in the circulatory system, provide improved sound reflection and image clarity. Microbubble-type imaging agents consist of minute bubbles of a gas (usually air) which are dispersed in a carrier liquid for parenteral injection. The "microbubbles" are carried by the circulatory system to the organ being imaged.

It has been proposed to form a dispersion of air microbubbles in a warm aqueous gelatin solution, and cooling the solution to a solidification temperature to trap the microbubbles. For administration, the gelled dispersion is to be warmed until it liquifies, and parenterally administered with the microbubbles dispersed in the liquified gelatin. (Tickner, et al. U.S. Pat. No. 4,276,885; and Tickner, et al., National Technical Information Service Report HR-69217-1A, April 1977). Gelatin-trapped microbubbles on introduction into the bloodstream have a short lifetime. They rapidly dissipate. Another disadvantage is that the microbubbles are too large to pass through capillary beds, and are therefore not suitable for heart imaging by peripheral intravenous administration.

The discovery by Dr. Steven B. Feinstein of sonicationproduced microbubble imaging agents represented an important advance in this art. Using viscous aqueous solutions, such as 70% sorbitol or dextrose, Dr. Feinstein produced a dispersion of microbubbles by high energy sonication of the solutions. The resulting microbubbles had sizes less than 10 microns, and were capable of passing through capillary beds. The persistence of the microbubbles, although of the order of a few minutes, permitted the imaging agent to be prepared and administered intravenously for heart imaging. (Feinstein, et al., 1984; and Feinstein U.S. Pat. No. 4,572,203.)

Subsequently Dr. Feinstein sought to improve the persistence of the microbubbles. He found that by sonication of a heat-sensitive protein, such as albumin, microbubbles of improved stability were obtained (Feinstein U.S. Pat. Nos. 4,572,203 and 4,718,433). Concentrations of microbubbles of 10 to $14 \times 10^6$ microbubbles per milliliter were obtained with bubble sizes from 2 to 9 microns (Keller, Feinstein, and Watson, 1987). The microbubbles persisted for 24 to 48 hours. However, the sonicationproduced albumin microbubble imaging of Feinstein was not sufficiently stable for commercial manufacture.

Stabilities of the order of weeks or months (rather than hours or days) are required to permit an imaging agent to be manufactured at a central location and distributed to hospitals in the United States and other countries. For commercially feasible manufacture, shipment and hospital storage prior to use, a stability time of at least four weeks is needed and preferably at least eight weeks, or longer. Also, for the most effective imaging, it is desirable to have the highest obtainable concentration of microbubbles in the imaging agent. An imaging agent of very high microbubble concentration is inherently better, and a safety factor is provided. These advances in the sonication generation of albumin encapsulated microbubbles have been partially achieved by Molecular Biosystems, Inc., San Diego, Calif. The experimental "ALBUNEX" product of this company comprises microspheres having microbubble centers with insolubilized albumin walls.

Prior to the present invention, however, the "ALBUNEX" microspheres have only been prepared in small quantities on a batch-by-batch basis. It was not known whether large scale commercial production was feasible. No one knew how microbubbles encapsulated with albumin could be produced on a continuous basis while obtaining size control, high microbubble concentration, and long-term stability.

SUMMARY OF INVENTION

This invention provides a sonication method for continuously producing microspheres comprising protein encapsulated microbubbles in controlled small sizes, effective concentration ranges, and commercially and clinically practical stabilities. As in prior practice, a dilute aqueous solution of a heat-denaturable, water-soluble, biocompatible protein is prepared. For example, as in prior practice, a sterile 5% aqueous solution of human serum albumin can be used. For continuous production, it has been found to be critical to rapidly heat increments of the protein solution to a temperature of incipient denaturation for the protein. An indirect flow-through heat exchanger can be used for this purpose, but it is important that the temperature of the heat exchange liquid medium be carefully controlled. Essentially the heat exchange medium should be at the desired incipient denaturation temperature. At the conclusion of the rapid heating step, the protein solution is on the verge of denaturation but should not contain denatured protein. The heating to the temperature of incipient denaturation is carried out without appreciable protein insolubilization.

Another critical feature of the process is to introduce a biocompatible gas into the protein solution. Sterile air is preferably employed for this purpose. The introduction of air provides an excess of air for formation of the microspheres. Air addition can be carried out before, during, or after the heating. In a preferred procedure, however, the gas is introduced immediately following the heating, concurrently with the introduction of the heated solution into the sonication chamber.

The gas-containing heated increments of protein solution are continuously passed through a chamber enclosing an operating sonicator, which provides a sonicator horn in contact with the solution. The sonication produces gas microbubbles in the solution while the protein therein is quickly heated to insolubilize protein around the microbubbles. Since the solution has already been heated to a temperature of incipient denaturation, only a few degrees of additional heating is required to produce the insolubilized protein, which forms the walls of the microspheres.

The formation of a large population of minute microbubbles (less than 10 microns in diameter) takes place with extreme rapidity due to the excess air present in the solution. The insolubilized albumin is formed with equal rapidity because of the preheated condition of the solution. These factors result in extremely rapid formation of the protein-encapsulated microbubbles, referred to herein as "microspheres". The residence time of a solution increment in the sonicator chamber can be very brief.

By the method of this invention it is possible to form the microsphere imaging agent on a continuous, high-production basis. The solution as discharged from the sonication chamber already contains the stable, small size, protein-encapsulated microspheres. Only a small amount of oversize or undersize microspheres are present. This eliminates the need for any time consuming fractionations. Intense foaming of the solution occurs during the sonication, and the solution as discharged from the sonication chamber will have a foamy character. But the foam can be easily dissipated.

THE DRAWINGS

The sonication method of this invention for continuous production of albumin encapsulated microbubbles can be carried out in a sequence of operations. These operations are illustrated diagrammatically by the accompanying drawings, in which—

DETAILED DESCRIPTION

Figure 1:
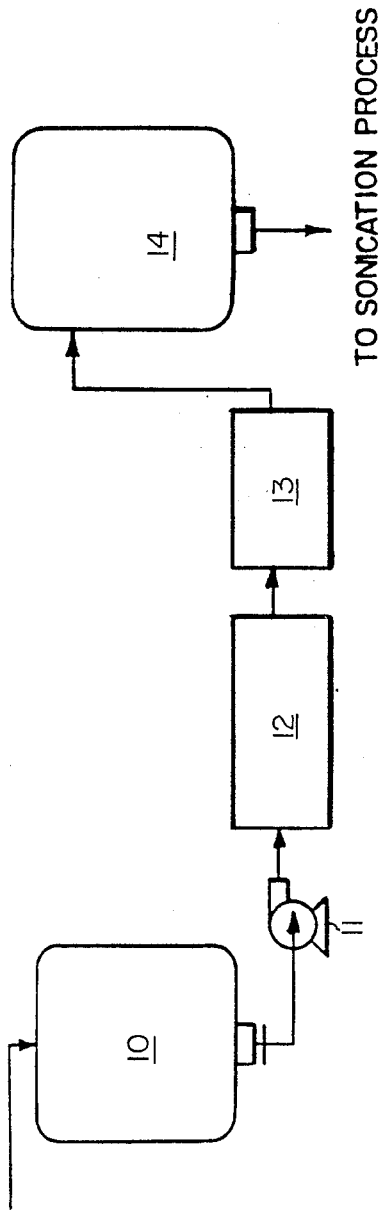
FIG. 1 is a flow sheet illustrating the preparation of the albumin solution.

The starting material for practicing this invention is an aqueous solution of a heat-denaturable, water-soluble biocompatible protein. The encapsulating protein should be heat-sensitive so that it can be partially insolubilized by heating during sonication. More specifically, coincident with the sonication, a small portion of the dissolved protein material is insolubilized. This results in a small volume of solid phase material, which forms the encapsulating layers around the microspheres. Heat-sensitive proteins may be used such as albumin, hemoglobin, collagen, etc. For administration to humans, human protein is preferred. Human serum albumin (HSA) is especially suitable. HSA is available commercially as a sterile 5% aqueous solution, which can be used directly as the starting material for preparing the microspheres. However, other concentrations of albumin or other heat-denaturable proteins can be used. HSA concentration can be varied, for example, within the range from 1 to 25% by weight. In the continuous process of the present invention, it is desirable to utilize the protein in the form of a dilute aqueous solution. For albumin, it is preferred that the solution contain from 0.5 to 7.5% by weight of the albumin. Because of the extremely favorable conditions established for microbubble generation, protein insolubilization, and resulting encapsulation, concentrations within 5% albumin may be used, such as from 0.5 to 3%.

Commercially-available equipment may be used in pracicing this invention. The feed preparation operation utilizes stainless steel tanks and process filters which can be obtained from Walker Stainless Equipment Co., New Lisbon, Wis., and Milliporr, Bedford, Mass., respectively, as well as other companies. This operation insures that all feed media to be sonicated will be consistent with FDA requirements and regulations.

The sonication operation utilizes both a heat exchanger and a flow through sonicating vessel, in series. Heat exchanger equipment of this type can be obtained from ITT Standard, Buffalo, N.Y., and other companies. The heat exchanger maintains operating temperature for the sonication process. Its temperature control of the sonication media ranges from 65° C. to 80° C., depending on the media's makeup.

Sonication equipment's vibration frequencies can vary over a considerable range, such as from 5 to 40 kilohertz (kHz), but most commercially-available sonicators operate at 20 kHz or 10 kHz. The 20 kHz sonicators perform well for purpose of this invention. Such sonicating equipment can be obtained from Sonics & Materials, Inc., Danbury, Conn., and other companies. Sonics & Materials Vibra-Cell or similar model can be used with a flat tip sonicator horn. The power applied to the sonicator horn can be varied over power settings scaled from 1 to 10 by the manufacturer, as with Sonics & Materials Vibra-Cell Model VL1500. An intermediate power setting can be used (viz. from 5 to 9). The vibrational frequency and the power supplied must be sufficient to produce cavitation in the liquid being sonicated. Feed flow rates range from 50 ml/min to 1000 ml/min. Residence times in the sonication vessel can range from 1 sec to 4 mins. Gaseous fluid addition rates range from 10cc/min to 100cc/min or 5% to 25% of the feed flow rate.

Sonication is deliberately carried out in such manner as to produce intense foaming of the solution, contrary to conventional sonications, where it is desirable to avoid foaming. For the purpose of the present invention, foaming and aerosolating are important for obtaining the imaging agent of enhanced concentration and stability. To promote foaming, the power input to the sonicator horn may be increased, as well as operating the process under slight pressure (i.e., 1-5 psi). The foaming produced from the sonication is immediately detectable by the cloudy appearance of the solution, and by the foam produced.

By means of the continuous sonication process, comprising the cavitation phase followed by a foaming phase, the concentration of the encapsulated microbubbles, referred to herein as "microspheres", can be greatly increased. Concentrations in excess of $40 \times 10^6$ microspheres per milliliter are easily obtainable, such as from 40 to $200 \times 10^6$ concentrations. Moreover, the resulting microspheres will be predominately of diameters less than 10 microns. For example, 80% or more of the microspheres can have diameters in the range from 1 to 9 microns with a mean diameter of 4 to 6 microns.

When the sonication is carried out in contact with air as the gaseous fluid, the microsperes will have air centers. Air is believed to be the most convenient gaseous fluid, but if desired sonication could be carried out under other gaseous fluids (viz., nitrogen, oxygen, carbon dioxide, etc.).

The continuous sonication process allows for a continuous or at least a semi-continuous separation/concentration operation. Again a stainless steel tank/vessel can be obtained from Walker Stainless Equipment Co., New Lisbon, Wis., or other companies. The separation/concentration operation allows for total control of the product output in terms of microsphere concentrations and overall mean sphere size.

Since microspheres are buoyant they tend to rise to the surface of the dispersion. By holding the dispersion without agitation for a number of hours (viz. for 1 to 8 hours), most of the microspheres will rise to the surface and concentrate in an upper layer above the clarified solution. By this separation/concentration operation or "float-separation" of the microspheres into an upper layer, portions of the clarified solution can be removed from below the microspheres, thereby obtaining a dispersion of greater microsphere concentration. For example, from 50 to 75% of the solution volume may be removed in this concentration process. This clarified solution may be recycled back to the feed preparation operation.

If needed, either before or after the above-described concentration, float-separation of oversized microspheres can be obtained. Large size microspheres such as one having diameters greater than 10 microns have relatively greater buoyancy. They will therefore rise more rapidly to the surface of the solution. By utilizing a short holding time, such as from 15 to 45 minutes, the largest size microspheres can be selectively collected in a small upper layer above a dispersion which will still contain substantially all of the microspheres of small size. By removing this microsphere dispersion from beneath the layer of oversize microspheres, a fractionation may be achieved in which the larger microspheres will remain in the vessel in which the fractionation is carried out. However, the inherent size control obtained by the continuous sonication of this invention makes it unnecessry to carry out lengthy separation steps for removal of over or under size microspheres.

The imaging agent produced by this combination of continuous sonication and the separation/concentration can have a homogeneously-dispersed concentration of greater than $200 \times 10^6$, such as from 100 to $1200 \times 10^6$ (1 to $12 \times 10^8$) microspheres per milliliter. High concentrations can be maintained for long periods of holding at ambient room temperatures (20°-25° C.). Concentrations above 200 and typically above $400 \times 10^6$ microspheres per milliliter can be maintained for periods of at least four and usually eight weeks or longer.

ILLUSTRATIVE EMBODIMENTS

Figure 2:
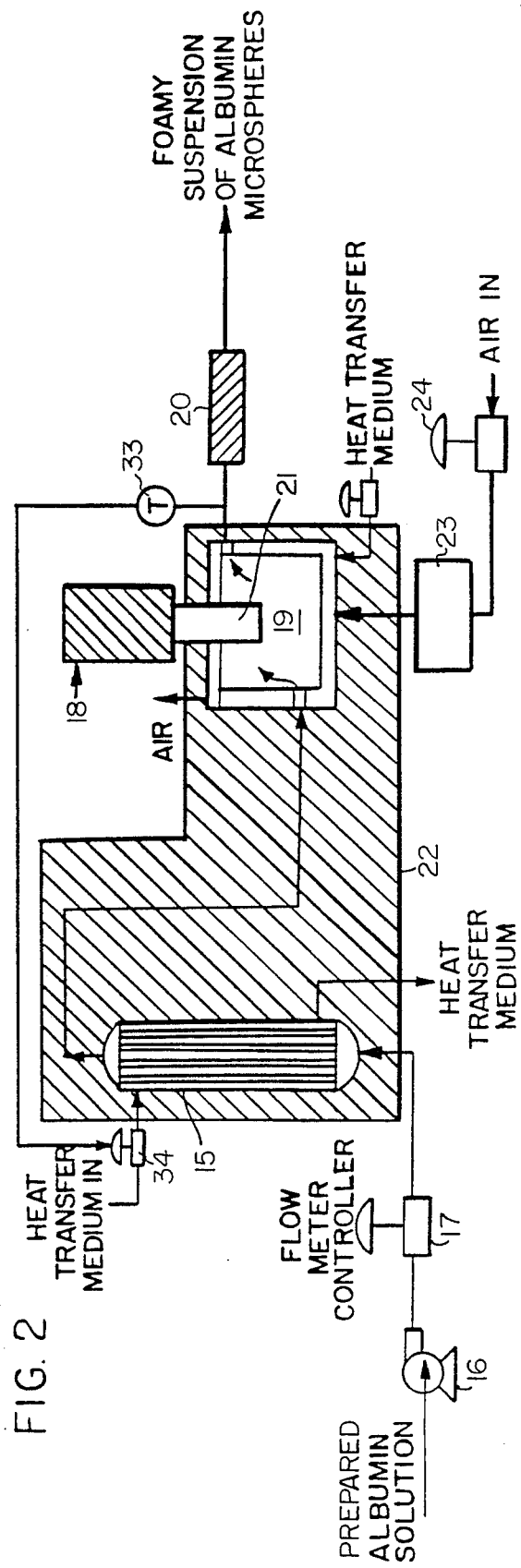
FIG. 2 is a diagrammatic flow sheet of the sonication operation, including the preheating, air introduction, and continuous sonication.
Figure 4:
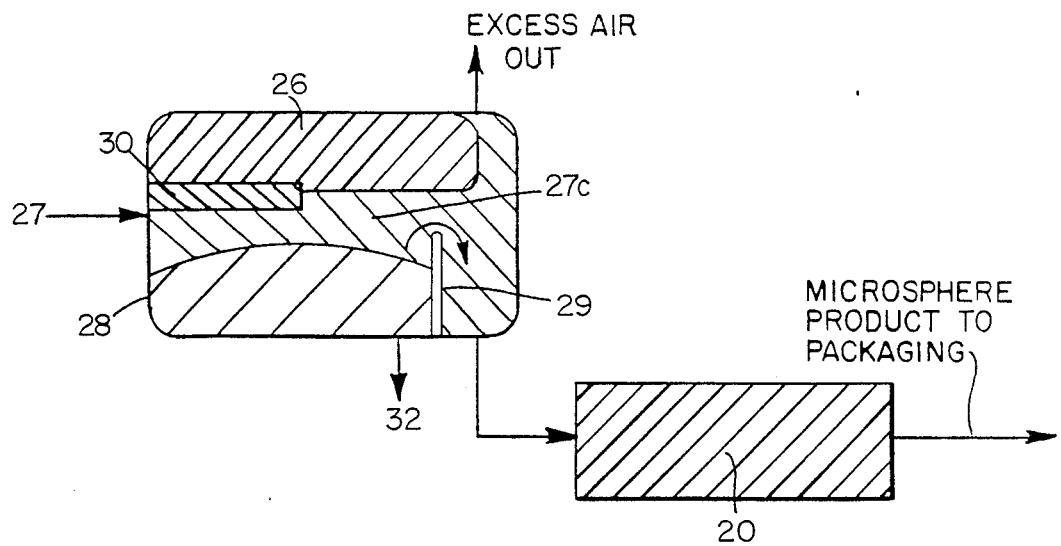
FIG. 4 is a flow sheet illustrating the further processing of the suspension of albumin microspheres in a separator/ concentrator.

FIGS. 1, 2 and 4 illustrate the three operations of a manufacturing plant for producing the microsphere imaging agent. The feed medium, comprising the albumin solution, is first subjected to a feed preparation operation. The medium is then transported to the sonication operation. After, the medium is heated and a gaseous fluid is added, the medium is sonicated. It is then transported to a separation operation, where the microspheres are concentrated. The clarified medium can be removed from the microsphere suspension, and recycled back to the feed preparation operation.

FIG. 1 details the feed preparation. The feed medium is pumped through a series of filters to validate the feed medium under FDA specifications. The filtered medium is then placed in one or more feed tanks for the sonication operation.

FIG. 2 details the sonication operation. The medium is passed through a flow control valve and a heat exchanger before entering the sonication vessel. A gaseous fluid, preferably air, is introduced into the feed medium either at or before the sonication vessel at a controlled rate. For example, air may be supplied from a pressurized source, such as bottled compressed air, or supplied by an air pump. The air should be in sterilized condition before it is added to the solution.

FIG. 4 details the separation and concentration operation. Here the microspheres are concentrated by float-separation at or near the top of the vessel, which may contain a static defoamer as shown. This defoamer can also serve to disrupt large size microspheres which are floating on top of the solution. The microsphere concentrate is selectively removed. The clarified medium in the bottom of the separator can be transported back to the feed preparation operation and recycled. In this recycling, all solid material and particles are removed, leaving only the protein in solution.

FIG. 2 illustrates the operation which is the heart of the process. As indicated an insulation jacket surrounds the heat exchanger and sonicator vessel. The prepared albumin solution is pumped through a flow meter controller into the feed end of the tube and shell heat exchanger. In the heat exchanger, the albumin solution passes through multiple tubes which extend to the discharge end of the exchanger. These tubes may be double jacketed to assure separation from the heat transfer medium, which enters the space surrounding the tubes near the discharge end, and flows countercurrently to the albumin solution before discharge near the feed end of the exchanger. Suitable liquid heat transfer media are water and mineral oil.

The temperature of the heat transfer medium is carefully controlled to a temperature corresponding to the target incipient denaturation temperature of the albumin. For human serum albumin, the incipient denaturation range is between 70° C. and 75° C. Temperatures above 75° C. can result in substantial insolubilization of the albumin. A desirable operating range for the heat transfer medium is from 72° to 74° C. The albumin solution is heated rapidly with a single pass through the heat exchanger from an inlet temperature of 20° to 30° C. to an outlet temperature of 72° to 73° C. In practice, the residence time in the heat exchanger can be less than one minute, such as from about 45 to about 55 seconds.

As shown in FIG. 2, after rapid heating to an incipient denaturation temperature for the albumin, the solution is passed to the inlet of a jacketed sonication vessel. This vessel may be of small volume, such as from 25 to 400 liters. In the vessel, there is mounted a sonicator horn for direct contact with the solution as it flows through the vessel. Into the bottom of the vessel there is introduced a continuous flow of sterile, filtered air or the sonication proceeds. The air is dispersed in the solution, and rapidly formed into microspheres. The temperature of the solution in the sonicator is raised a few degrees above its entry temperature, the increase being sufficient to insolublize a portion of the albumin. For example, from 0.5 to 3% of the albumin introduced into the vessel may be denatured and thrown out of solution to provide the encapsulating protein. Under steady flow conditions, the control temperatures of the solution in the sonication vessel can be 74° C. ±0.2. The suspension of microspheres as discharged from the sonication vessel will have this temperature, which may be sensed by a temperature controller, using a feedback to a regulator for the flow rate of the heat transfer medium.

The removed foamy suspension of the microspheres can be passed through a static mixer, but this is optional. If used the static mixer can begin to break up the foam, and provide a homogeneous dispersion of the microspheres. As shown in FIG. 4, the foamy suspension is passed to a separator and concentrator unit which includes a static defoamer. The microspheres are removed with the solution flowing over the top of the weir. The defoamed solution is removed and passed through a static mixer. The mixer assures that the microspheres are homogeneously dispersed in the solution.

Preparation of the imaging agent is complete at this point. Albumin microspheres of the desired size are within the range from 1 to 10 microns. For example, they may be predominately sized from 3 to 8 microns. The microsphere concentrate preferably has a concentration in the range from 400 to 800 $10^6$ microspheres per milliliter. The suspension of the microspheres may be packaged in suitable vials under sterile conditions for subsequent administration as an ultrasonic imaging agent.

Figure 3:
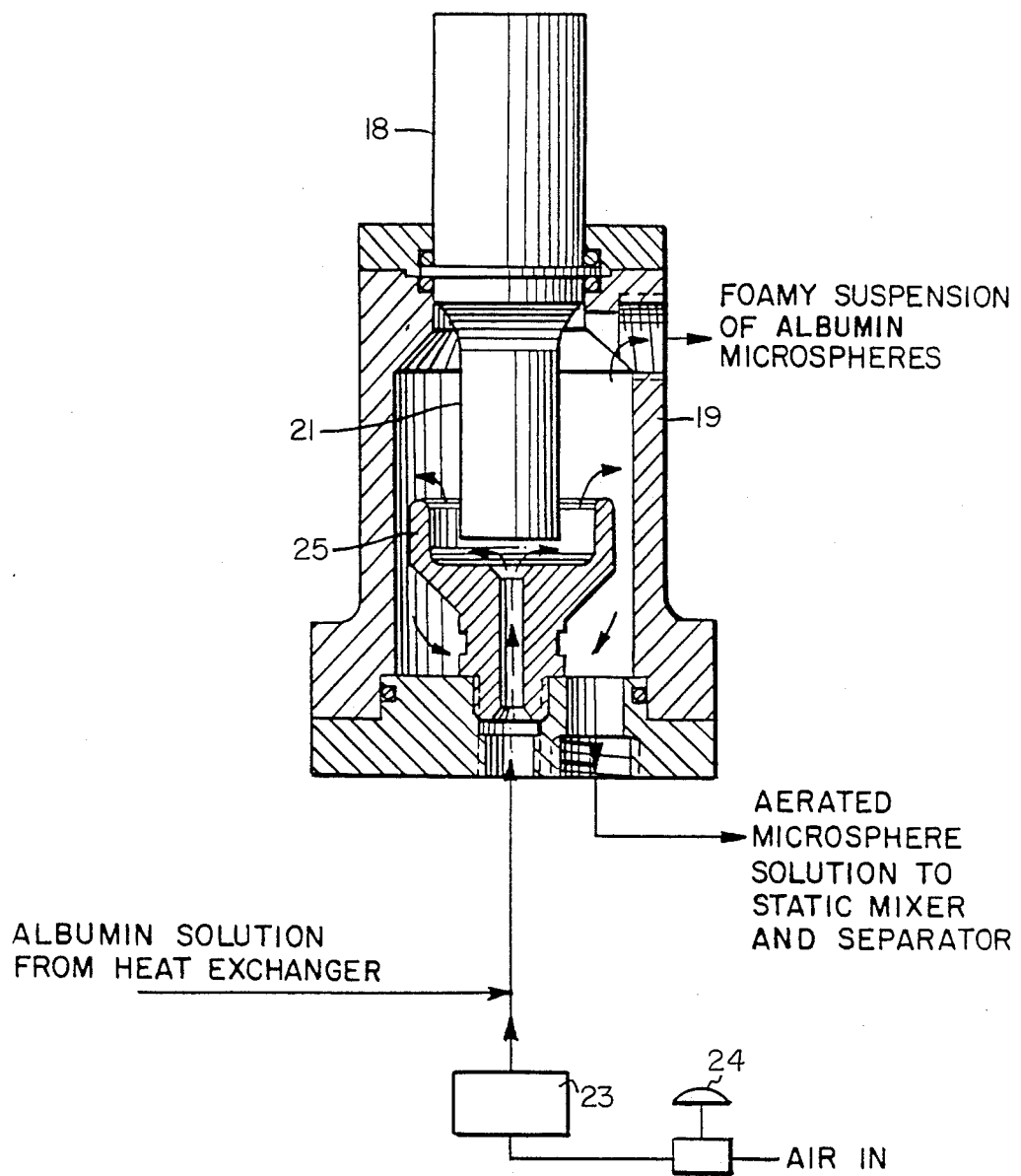
FIG. 3 is an enlarged cross-sectional view of a sonicator which may be used instead of the sonication vessel of FIG. 2.

FIG. 3 illustrates an alternate sonication apparatus. Similar sonicator units are obtainable from Sonics & Materials, Danbury, Conn. A small size chamber can be provided, which may have an internal volume of about 50 to 150 cc. The sonicator provides a horn which extends into the sonication chamber, and the chamber has a cavity-providing wall portion, which as shown is in the form of a cup. This cup is arranged in closely-spaced opposed relation to the sonicator horn. The sonicator horn may extend into the cavity of the sonicator cup. Through a passage extending into the bottom of the sonicator cup, a premixed air/ albumin solution is introduced. The albumin solution has been passed through the heat exchanger, as previously described, and the air is introduced from a source of pressurized air under sterile conditions. The residence time of the solution in the sonicator can be very short, such as of the order of 1 to 20 seconds. The foamy suspension of albumin microspheres as discharged from the sonication chamber is processed as previously described with reference to FIGS. 2 and 4.

Figure 5:
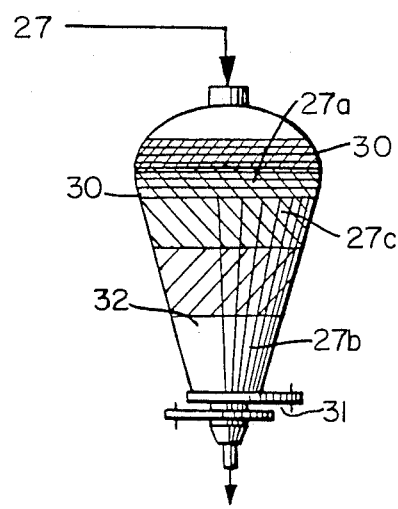
FIG. 5 is an alternate separator/concentrator which may be used instead of the apparatus illustrated in FIG. 4.

In FIG. 5, there is shown an alternate separator/concentrator in the form of a funnel-shaped vessel equipped at its bottom with a valve-controlled outlet. A series of such separatory funnels may be used, permitting increments of the foamy microsphere suspension to be held for defoaming and size separation. The foam collects on top of the solution together with oversize microspheres. Undersize microspheres concentrate toward the bottom of the funnel, and can be removed together with the albumin solution to be recycled as the first drainage fraction from the funnel. The next fraction will comprise the albumin microspheres which are passed to a static mixer, as previously described, and then to packaging. The final fraction removed from the separatory funnel will comprise the residual foam and oversize microspheres, and is discharged to waste.

OPERATING PROCEDURES

Feed Preparation

Fill the 100 or 200 liter feed tanks with aqueous albumin, 5%. Pump the albumin through the filters at rates between 50ml/min to 1L min. The filter albumin is placed in the sonication operation's feed tanks.

Sonication

A controlled flow of albumin, between 50 ml/min and 1 liter/min, is transported through a heat exchanger, equipped with a feedback temperature control loop designed to control the albumin temperature during the sonication process. The temperatures of the heat transfer medium and the heated solution are as previously described. A filtered gas (i.e., air at 25cc/min to 200cc/min) is added to the sonication process. This air greatly enhances cavitation and formation of microbubbles during the sonication process. Using a sonication vessel as shown in FIG. 2, the total residence time in the sonication vessel is between 1.0 and 4 minutes. The sonication power (or energy) setting can be set at a range of 6 to 10 (on a scale of 1 to 10). The static mixer after sonication defoams the less dense foam. Optionally, the sonication product may be placed in a holding tank and mixed before proceeding to separation operation.

Separation/Concentration

The sonication operations product settles out between 1-8 hours without agitation in a separator/concentrator vessel. When substantially all the microspheres have formed a layer on the top, drain approximately two-thirds of the volume from the bottom. The top layer is microsphere product. The bottom layer is returned to the feed preparation operation to be recycled.

Optional Fractionation

Resuspend the microspheres and fill a 60 ml syringe with them. Let sit 30 minutes, then drain all but about the last 3-4 ml into a collection vessel. The oversize microspheres are left. Count a sample and calculate the concentration, mean diameter, and percentage less than 10 microns. If less than 90% are less than 10 microns, re-fractionate. If required for redispersion, the concentration may be adjusted with 5% human serum albumin.

REFERENCES

Feigenbaum, et al. (1970), *Circulation* 41:615–521
Feinstein, U.S. Pat. No. 4,572,203.
Feinstein, U.S. Pat. No. 4,718,433.
Feinstein, et al. (1984), *J. Am. Coll. Cardiol.* 3:14–20.
Gramiak and Shah (1968), *Invest. Radiol.* 3:356–358.
Keller, Feinstein and Watson (1987), *Amer. Heart J.*, 114:570–575.
Tickner et al. U.S. Pat. No. 4,276,885.
Tickner, et al., National Technical Information Service Report HR 62917-1A, April, 1977, pages 34–40.

We claim:

1. The method of producing an imaging agent for diagnostic use in the human circulatory system in which an aqueous solution of human serum albumin in subjected to sonication to form minute gas-center microspheres, wherein the improvement comprises:
   (a) prior to sonication rapidly heating an aqueous solution of human serum albumin to a temperature of incipient denaturation of albumin;
   (b) dispersing a biocompatible gas in said heated solution;
   (c) flowing the gas-containing heated solution through a chamber enclosing an operating sonicator which provides a stationary horn immersed in the solution as it passes through said chamber; and
   (d) with a solution residence time in said chamber of from 1 to 20 seconds forming microspheres of less than 10 microns diameter at concentrations in excess of $40 \times 10^6$ microspheres per milliliter of solution, the stability of said microspheres being such that said solution maintains said excess concentration for over 8 weeks at 20° to 25° C.

2. The method of claim 1 in which the solution subjected to said sonication has an albumin concentration of from 0.5 to 7.5 percent by weight.

3. The method of claim 1 in which the solution subjected to sonication has an albumin concentration of around 5 percent by weight.

4. The method of producing an imaging agent for diagnostic use in the human circulatory system in which an aqueous solution of human serum albumin is subjected to sonication to form minute air-center microspheres, wherein the improvement comprises:
   (a) prior to sonication rapidly heating an aqueous solution of human serum albumin to a temperature in the range from 70° to 75° C. without denaturing the albumin, said solution having an albumin concentration of from 0.5 to 7.5 percent by weight;
   (b) dispersing air in said heated solution;
   (c) flowing the air-containing heated solution through a chamber enclosing an operating sonicator which provides a stationary horn immersed in the solution as it passes through said chamber; and
   (d) with a solution residence time in said chamber of from 1 to 20 seconds forming microspheres predominately sized in the range from 3 to 8 microns diameter, said microspheres being formed at concentrations in excess of $40 \times 10^6$ microspheres per milliliter of solution, the stability of said microspheres being such that said solution maintains said excess concentration for over 8 weeks at 20° to 25° C.

5. The method of claim 4 in which said solution has an albumin concentration around 5% by weight, and said heating in step (a) is to a temperature of approximately 74° C.

6. The method of claim 4 and 5 in which said microspheres as produced in steps (c) and (d) have means diameters in a range from 4 to 6 microns, and the microspherecontaining solution has a concentration in excess of $400 \times 10^6$ microspheres per milliliter.

* * * * *